United States Patent
Kukal et al.

(10) Patent No.: US 6,519,953 B1
(45) Date of Patent: Feb. 18, 2003

(54) METHOD FOR USE OF LATENT HEAT TO MAINTAIN SELECTABLE COLD STORAGE TEMPERATURES

(76) Inventors: Olga Kukal, 1 Prince Street, Dartmouth, Nova Scotia (CA), B2Y 4L3; Thomas Allen, 1 Prince Street, Suite 705, Dartmouth, Nova Scotia (CA), B2Y 4L3

(*) Notice: Subject to any disclaimer, the term of this patent is extended or adjusted under 35 U.S.C. 154(b) by 0 days.

(21) Appl. No.: 09/960,950

(22) Filed: Sep. 25, 2001

(51) Int. Cl.[7] .............. B65B 63/08; F25D 3/08; F25D 3/10; F25D 11/00; C09K 5/00; C12N 5/02
(52) U.S. Cl. .............. 62/60; 62/371; 62/529; 62/530; 62/430; 62/457.1; 252/71; 435/374
(58) Field of Search .............. 62/60, 371, 529, 62/530, 430, 457.1, 457.2, 457.7, 457.9; 252/71; 435/374

(56) References Cited

U.S. PATENT DOCUMENTS

| | | | | |
|---|---|---|---|---|
| 3,974,658 A | * | 8/1976 | Starrett | 206/427 |
| 4,596,250 A | * | 6/1986 | Beisang et al. | 607/114 |
| 4,856,294 A | * | 8/1989 | Scaringe et al. | 165/46 |
| 4,903,493 A | * | 2/1990 | Van Iperen et al. | 206/306 |
| 4,986,076 A | * | 1/1991 | Kirk et al. | 62/294 |
| 5,435,142 A | * | 7/1995 | Silber | 422/939 |
| 5,444,989 A | * | 8/1995 | Gawron et al. | 62/129 |
| 5,770,295 A | * | 6/1998 | Alderman | 126/618 |
| 5,804,444 A | * | 9/1998 | Kukal et al. | 435/374 |
| 5,976,400 A | * | 11/1999 | Muffett et al. | 252/70 |
| 5,983,661 A | * | 11/1999 | Wiesman | 62/371 |
| 6,209,343 B1 | * | 4/2001 | Owen | 252/67 |
| 6,266,972 B1 | * | 7/2001 | Bostic | 62/371 |

OTHER PUBLICATIONS

Becker, et al., General Chemistry, 1973, pp. 406–407, Houghton Mifflin Co., Boston
Berry, et al., Physical Chemistry, 1980, pp. 924–928, John Wiley & Sons, New York.

* cited by examiner

Primary Examiner—William C. Doerrler
Assistant Examiner—Filip Zec
(74) Attorney, Agent, or Firm—Fulbright & Jaworski, LLP

(57) ABSTRACT

A method for maintaining selectable cold storage temperatures for protracted periods of time using pre-mixed thermal control materials having predetermined melting temperatures equal to the selectable cold storage temperatures is provided. According to preferred embodiments, the thermal control materials are solutions that are filled into cold packs and the solutions are frozen to maintain selected temperatures less than 0° C. The present invention includes methods of storage and transport of materials using the cold packs.

13 Claims, 2 Drawing Sheets

METHOD FOR USE OF LATENT HEAT TO
MAINTAIN SELECTABLE COLD STORAGE
TEMPERATURES

BACKGROUND OF THE INVENTION

1. Field of the Invention

The present invention relates to unfrozen cold storage of perishable materials. More particularly, the present invention relates to packs, which incorporate thermal control material, capable of maintaining perishable biological materials that are in contact with or are enclosed by the packs at selectable temperatures, including sub-zero degree centigrade ("C.") temperatures, for protracted periods of time.

2. Description of the Related Technology

It is known that perishable materials especially biological materials, e.g., food, flowers, pharmaceuticals, etc., can be stored at temperatures reduced from those at ambient to decrease rates of deterioration for extended periods of time. Reduced temperatures inhibit, for example, the activity of degradation enzymes indigenous to many biological materials as well as inhibit the growth of microorganisms. Currently practiced methodologies of reduced temperature storage can be divided into two categories: 1) storage of materials in an unfrozen state; and 2) storage of materials in a frozen state. When stored unfrozen, materials now generally are refrigerated or maintained at temperatures between 0° C. and 10° C. Alternatively, materials, when stored in a frozen state, customarily are stored at temperatures of −15° C. or less. These practiced methodologies do not normally utilize the temperature range between about 0° C. and −15° C.

Existing cold storage methods and technologies suffer from serious defects. For example, with unfrozen storage, the temperature reductions into the 10° C. to 0° C. range slows enzymatic degradation and microbial growth in biological materials, but does not stop these processes completely. Thus, maintaining biological materials at temperatures between 0° C. and 10° C. will extend storage times, but such extensions are actually limited in duration from what is now known to be feasible, as is discussed below. Some biological materials stored at temperatures from 0° C. and above, such as RNA and mixed pharmaceutical test reagents, begin to undergo a noticeable amount of deterioration in as short a period as one or two days, and can become completely unusable after two or more days. As is generally appreciated, short storage times place major constraints on the availability of fresh, non-frozen materials such as foodstuffs and/or other biological materials, such as vaccines and other biomedical materials. In essence, these materials must be obtained or produced in close proximity to where they will be sold or used in order to provide commercially practical storage times after shipping.

Freezing biological materials overcomes some of the deleterious consequences inherent in shipping fresh materials at unfrozen temperatures. For example, once frozen, biological materials may be stored for protracted periods during which they can be shipped over long distances, because freezing essentially stops enzymatic and microbial degradation processes. However, ice crystals unavoidably form within the biological materials during freezing, these crystals can damage the materials. Specifically, the formation of ice crystals can destroy the cellular integrity of the materials or cause "freezer burn." As is generally appreciated, the consequential damage to biological materials resulting from freezing reduces the quality of the thawed materials. In particular, with many foodstuffs, for example, the reduction in the quality caused by freezing results in reduced palatability and a corresponding reduction in the commercial value of the food relative to that same food in a fresh, unfrozen state.

In U.S. Pat. No. 5,804,444 (the "'444 patent") to Kukal and Allen (the same inventors as here), which is hereby incorporated by reference in its entirety, the present inventors disclose novel technology for storing any biological material in an unfrozen state by determining the optimum storage temperatures for biological materials so as to overcome many of the limitations of prior storage methodologies. This novel technology is based on an appreciation of the fact that most biological materials have distinct sub-zero ° C. melting point depressions. By determining the melting point depression for a given biological material and then storing that material at its optimum storage temperature, which is slightly greater than but as close to the melting temperature as feasible, very substantial improvements in the duration and quality of the stored non-frozen biological material is achieved.

The discovery that biological materials have determinable lowest optimum storage temperatures at which they can be stored for extended periods of time has produced a need for refrigeration and packaging adapted to maintain biological materials at very stable temperatures just above the determined melting temperatures. These temperatures are predominantly below 0° C.

Currently known and available cold storage packaging materials, such as those called "cold packs" or "gel packs," are not capable of meeting these needs because they are not capable of being adjusted to maintain different specific temperatures required to achieve the improvements in storage of non-frozen biological materials described above. These known devices, i.e., "cold packs" or "gel packs", for storing biological materials at reduced temperatures generally fall into two categories: 1) those that function by absorbing sensible heat to preserve storage temperatures reduced from ambient; and 2) those that function utilizing a latent heat capacitance incorporated in the container to preserve a desired storage temperature. As used here, "sensible heat" is heat energy absorbed by a thermal control or temperature maintenance material that results in a corresponding increase in the temperature of the temperature maintenance material. Consequently, it is not feasible to maintain a desired temperature using a pack that functions by absorbing sensible heat, because as heat is absorbed the maintained temperature concomitantly increases. In contrast, "latent heat" is a determinable quantity of heat energy for a specified mass of a temperature maintenance material required to affect a phase transition in the material, e.g., from frozen to liquid states. During the phase transition the material maintains a substantially constant melting temperature. Latent heat equates to the amount of heat energy required to cause a given mass of solid material that is maintained at its melting temperature to become a liquid at that same temperature. Thus, the solid material continues to maintain a substantially constant temperature—its melting temperature—while external input heat energy is absorbed by the solid material to provide latent heat for affecting the process of melting.

An advantage in using latent heat when absorbing heat energy, as opposed to utilizing a sensible heat absorption process during corresponding warming, lies in the typically tremendous thermal capacitance associated with a material undergoing a phase change. In the case of water, one kilocalorie (1 Kcal) of heat absorbed as sensible heat is required to raise the temperature of one kilogram (1 kg) of the water by 1° C. Whereas, the same 1 kg of water in a solid ice state at 0° C. requires absorption of 144 Kcal of heat to affect the phase change to the liquid state for the water that remains at 0° C. throughout the phase change. Hence, 144 Kcal of heat can be absorbed by the 1 kg of ice which maintains a constant temperature of 0° C. In sum, utilization of latent heat permits absorption of increased amounts of heat energy while a melting temperature is maintained; whereas, absorption of sensible heat occurs over an unavoidable ever increasing dynamic range of temperatures.

Despite the advantages of using latent heat processes, there still are many drawbacks encountered when using currently available containers or packs employing latent heat to maintain constant temperatures. For example, these devices are not capable of providing selectable melting temperatures, and, thus, are not suitable for use in maintaining a range of biological materials at their distinct optimum storage temperatures. Furthermore, the current technology does not provide storage devices that are adapted for adjustment in order to change storage temperatures between storage uses. In other words, depending on what is being stored, different melting temperatures cannot be provided for different food products or other biological materials.

An example of such a prior device is the modular cold-storage pallet, including an insertable heat sink material utilizing latent heat, that is described in U.S. Pat. No. 6,266,972 to Bostic.

The foregoing underscores drawbacks and problems associated with conventional storage container and pack technology. In particular, the foregoing highlights problems associated with such devices, and their methods of use. Furthermore, the foregoing highlights the current, yet unresolved, need for storage containers capable of maintaining stable specific temperatures, in particular sub-0° C. temperatures. Also, the foregoing highlights the need for storage containers and packs that can be used to maintain biological materials at their optimum storage temperatures as taught in the '444 patent in unfrozen (fresh) states to maximize shelf lives and optimize quality.

SUMMARY OF THE INVENTION

The present invention overcomes the practical problems described above and offers new advantages as well.

The present invention is applicable to either thermal storage container or pack devices. As used here, thermal storage containers are intended to include any structure having curved sides, flat sides or a combination of all side shapes that can be in contact with or adjacent to stored materials placed in the containers. More specifically, containers usable with the present invention could be bowl shaped, open topped boxes, or closed topped boxes. Other configurations are, of course, feasible. Irrespective of the shape of a thermal storage container, the determinative aspect for any thermal storage container to be applicable to the present invention is that there be a capability to load a thermal control material such as a solution that can be frozen inside the structure of the container. Consequently, when heat is transferred from a stored material and its environment by conduction, convection, or radiation the transferred heat, or a significant portion of it, is absorbed by the frozen thermal control material to be utilized as latent heat in affecting melting of the frozen thermal control material. Generally, containers applicable to the present invention will have an interior compartment or compartments in which a thermal control material can be loaded. These compartments usually contain the thermal control materials so that they are not in direct contact with stored biological materials. In contrast, packs that are applicable to the present invention, in general, can be bag shaped devices which can be filled with a thermal control material such as a solution that can be frozen, or can be essentially rigid shaped devices having curved, flat, or a combination of such exterior surfaces. Again, the determinative aspect for a pack to be applicable to the present invention is that there be a capability to load a thermal control material that later can be frozen inside the pack. Hence, when heat is transferred from a stored material and its environment by conduction, convection, or radiation the transferred heat, or a significant portion of it, is absorbed by the frozen thermal control material to be utilized as latent heat in the melting process for the frozen thermal control material.

The present invention will be described below in the contexts of packs, but the descriptions are as applicable to container devices as described above and as such those containers are usable with and are within the scope of the present invention. These included containers, for example, can be multi-walled structures for storing processed or preprepared meals or food dishes, sometimes known of as Home Meal Replacements ("HMR"). Such containers can be used with thermal control materials of the present invention and after storage can be used as containers for heating or even serving the food. Additionally, the present invention will be described in the contexts of solutions for the thermal control materials, but any material capable of having selectable melting temperatures set is usable with and is within the scope of the present invention.

The solutions that are to be loaded into packs for the present invention are tailored to have specific melting temperatures selected to be the best temperatures for achieving extended storage times for materials to be stored statically or transported. As is discussed below such solutions can be solvent-solute, solvent-solvent, or other types of solutions that have had their melting points accurately tailored to preselected values, which are chosen to maximize storage times.

After a pack is loaded with a tailored solution the pack is subjected to below freezing temperatures to freeze the solution, and then the pack is allowed to thermally stabilize at the solution melting temperature for use in maintaining a stored material at its optimum storage temperature.

It is an object of the present invention to provide thermal control materials that melt at preselected temperatures that are optimum storage temperatures for materials being stored near the thermal control materials.

Another object of the present invention is to provide a storage container or pack filled with a thermal control material that has had its melting temperature tailored to a specific optimum storage temperature for a material being stored in the container or near the pack.

Yet another object of the present invention is to provide for refilling a storage container or pack with a changed thermal control material having an altered melting temperature so that a different material can be stored at its optimum storage temperature.

DETAILED DESCRIPTION OF THE INVENTION

Figure 1:
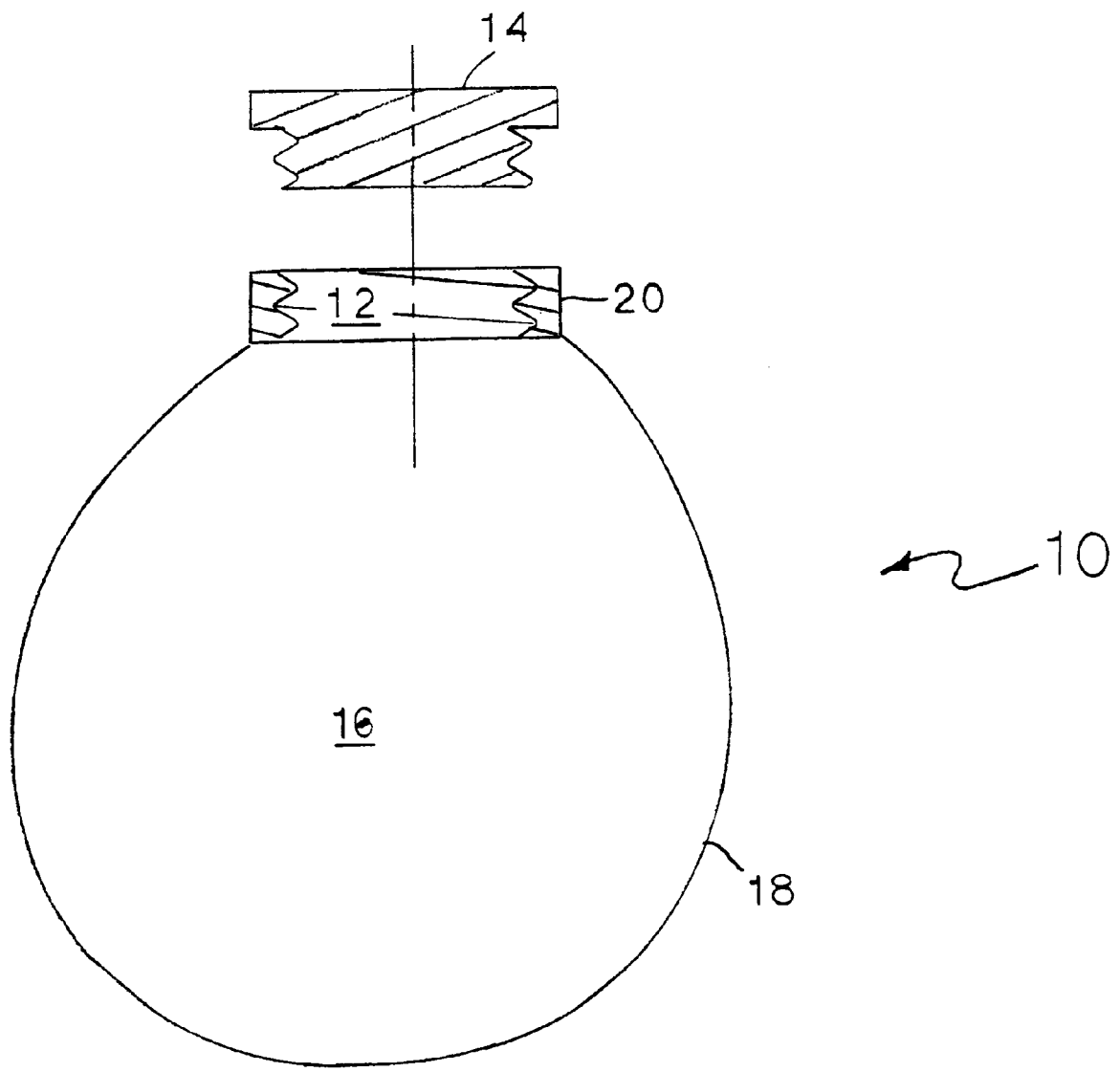
FIG. 1 is an exploded sectional view of one embodiment for a pack usable with the present invention.

Referring to FIG. 1, an exploded sectional view of an embodiment for a pack usable with the present invention is shown and is designated by the general reference numeral 10. This pack 10 includes an opening 12, a threaded cap 14, a fillable volume 16, and a flexible fluid tight bag 18 attached to a threaded ring 20 that forms opening 12. An ice bag can be used for pack 10. Variations of pack 10 that are within the scope of the present invention include use of preformed stiffbag material for bag 18 and a cap that is permanently welded, glued or otherwise sealed to the opening 12. All of these variations, and others that are apparent, are acceptable modifications that can be made to pack 10 and still provide a usable pack for the present invention. What must be provided irrespective of adaptable modifications is a fillable volume for a thermal control material that can be frozen and a sealable filling port. The pack must then be adaptable to being in proximity to a stored material so that heat can be transferred to the frozen thermal control material and the stored material can be maintained at an optimum storage temperature.

The thermal control material used to fill pack 10 is tailored to have a preselected melting temperature. As stated above thermal control materials will be described here in the contexts of preferred solutions, but other materials such as waxes, etc., are within the scope of the invention if they are capable of having their melting temperatures changed. A usable solution can be a solvent-solute or other types of solution. Whatever the solution type, it must be able to have its melting temperature adjusted over a range of temperature values. Solvent-solvent solutions can be of the aqueous antifreeze solution types such as ethyl alcohol-water, methyl alcohol-water, or propylene glycol-water which can, depending on the specific gravity of the solutions, have their melting temperatures adjusted. Similarly, solvent-solute solution types are unrestricted beyond the requirement of being able to adjust melting temperatures.

The preferred solution type is a solvent-solute solution, where water is the solvent. Other solvent-solute solution types are within the scope of the invention, e.g., benzene as a solvent and NaCl as a solute, but it is aqueous solutions that are preferred for their available melting temperature ranges below 0° C. The preferred aqueous solution types are further specified as being those having colligative solute properties that can be used to adjust melting temperatures; namely, adjustment of molality can be used to change solution melting temperatures. For example, melting will occur at a constant −1.86° C. for a frozen 1 kg water solution having one mole ("M") of dissolved solute. The relationship between the molality of such solutions and their melting temperatures is effectively a linear one up to when saturation is reached. Thus a 2 M water solution will have a −3.72° C. melting temperature, i.e., 2×−1.86° C. This linear relationship, i.e., molality times −1.86° C., has been referred to as van't Hoff's law of colligative properties and can be used to calculate the required molality of a water-solute solution for a preselected melting temperature.

It is an optimum temperature for storage of a specified material that should be selected for the solution melting temperature. As described in the '444 patent the optimum temperature for storage of a biological material is the lowest temperature at which the material may be kept without danger of freezing, which is a temperature close to, but above, the biological material melting temperature. The proximity to the biological material melting temperature can be a preferred 0.1° C. above that temperature. Therefore, preferred solutions for the present invention are mixed to molalities that ensure their having melting temperatures 0.1° C. above melting temperatures of stored biological materials. Other proximate temperature differences, e.g., 0.05° C., are within the scope of the present invention. At this time a difference of 0.1° C. has been found to be effective and is preferred.

An example for a particular biological material is chicken breasts which have a melting temperature of −1.2° C. In this instance, an optimum temperature for storage would be 0.1° C. higher which is −1.1° C. Using this optimum temperature for storage as a solution melting temperature, the required molality can be calculated using the van't Hoff law. The properly mixed solution can be filled into a pack, which is subjected to temperatures to freeze the solution. After freezing, the pack is allowed to thermally stabilize at the solution melting temperature and can be used to preserve chicken breasts.

The present invention has broad applicability to the static storage and transport of biological materials. Packs filled with frozen pre-mixed solutions are capable of maintaining optimum temperatures for storage even while biological materials are shipped using currently available transportation refrigeration systems that in fact may be several degrees warmer or more above the optimum temperature ranges for storage of each given product. In preferred embodiments, a high value item with a sub-zero optimum storage temperature, for example a material having an optimum storage temperature of −1.5° C., can be held at this temperature while transported in a refrigerated truck at +5° C. This present invention with its precise capabilities for stable optimum temperature control provides the maximum storage duration for unfrozen products, such as food, to be transported to consumers.

Moreover, the packs filled with frozen pre-mixed solutions may be utilized during retail display—e.g., in supermarket refrigerated display cases. Another advantage of the pack system of the present invention is a commensurate reduction of handling. For example, small fruits currently are harvested, stored in bulk in refrigerated warehouses, then packaged immediately prior to shipping. This requires repeated handling that can be reduced using packs of the present invention. The use of packs of the present invention in concert with using pre-mixed solutions having melting temperatures just above melting temperatures for storage can reduce handling in the following manner. The product when harvested is packaged for retail with packs placed in individual containers. The packs are prepared so that contained frozen solutions commence melting at a temperature above the melting temperature for the specific product, e.g., 0.2° C. The static storage facility (e.g., refrigerated warehouse) is set to maintain an optimum storage temperature which is 0.1° C. above the product melting temperature, but this is a temperature that is below the temperature at which the packs commence melting. When the product subsequently is shipped the included packs maintain an effective storage temperature during transportation that is 0.2° C. above the product melting temperature.

There are also extensive applications for packs of the present invention in the storage and transportation of vaccines, human tissues and organs. The packs of the present invention provide the ability to control and maintain optimum storage temperatures for any unfrozen biological material (e.g., fresh foods or biomedical supplies and substances) throughout a storage and/or transportation cold chain. The sub-zero ° C. packs of the present invention can maintain biological materials at their optimal temperature for storage even when the cold chain (i.e., the refrigeration systems from production through processing, transportation to retail or end-user) remain at currently conventional above zero degree C. temperatures.

A class of biological materials where accurate, stable cold storage temperature maintenance is critical are transplantable organs. When an organ is harvested from a donor's body, the clock begins to countdown the organ's life span. Storing and transporting the organ at a reduced temperature prolongs the organ pre-transplant life span, but does not prolong it enough to allow the organ to be revived in the body of a recipient if more than a few hours have passed. Thus, if a prospective recipient is outside a perimeter of a few hours travel time from the donor site, the organ will be of no use to the recipient. Therefore, it is crucial to provide as thermally stable a storage environment for pre-transplanted organs as is feasible. The present invention with its selectable solution melting temperature and use of latent heat to maintain a substantially constant temperature for extended periods satisfies these needs. In such cases, it may be necessary to use solutions having melting temperatures above 0° C. for the present invention. As is known such solutions can be prepared for example by using starch solutes.

The present inventors have determined that it is possible to transport vertebrate and invertebrate aquatic organisms or their organs/tissues at temperatures just above the onset of melting of their tissues including interstitial fluids in a state of suspended animation (bio-stasis). Examples of such vertebrate and invertebrate aquatic organisms include amphibians, fish, crustaceans, mollusks, cephalopods, echinoderms, arthropods, and their gametes, embryonic and larval forms. However, in order to maintain these organisms or their parts in bio-stasis, it is critical that they be maintained at precisely controlled temperatures that are specific to each species. Use of highly insulated containers, which are available from, for example, Delta Packing, Inc., Los Angeles, Calif., and temperature specific packs according to the present invention ensures that such organisms or their tissues can be globally transported in bio-stasis. Minor elevations of temperature, such as 0.3° C., during storage and transport can cause an organism to revive and die. Decreases in temperature below the specified optimal storage temperature can cause cold shock, freezing, cryoinjury and death. The thermal stability provided by packs according to the present invention where heat absorption supplies latent heat during substantially constant temperature phase transition is superior to the thermal environments available by using refrigeration systems alone because of unavoidable thermal fluctuations caused by refrigeration thermostat energized cooling and relaxation cycles. Furthermore, the packs of the present invention are relatively simple, inexpensive, and can be produced from biodegradable or recyclable materials.

Solutes used to prepare solutions for the present invention can be selected from the list of known colligative materials. They can be single compounds or a mixture of solutes, and can be food grade or non-food grade, or approved for biomedical or pharmaceutical applications.

Figure 2:
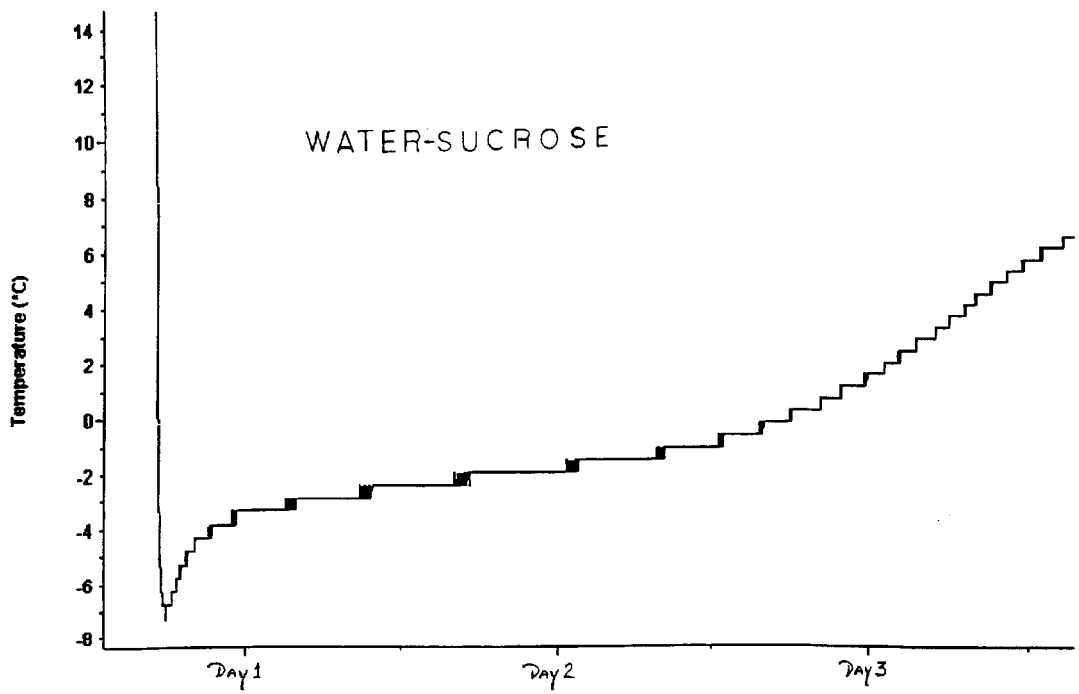
FIG. 2 is a graph showing the melting spectrum for a 1.2 molal water-sucrose solution as a function of time versus temperature about the solution melting temperature of −2.2° C.; and, FIG. 3 is a graph showing the melting spectrum for a 1.2 molal water-sodium bicarbonate solution as a function of time versus temperature about the solution melting temperature of −2.2° C.
Figure 3:
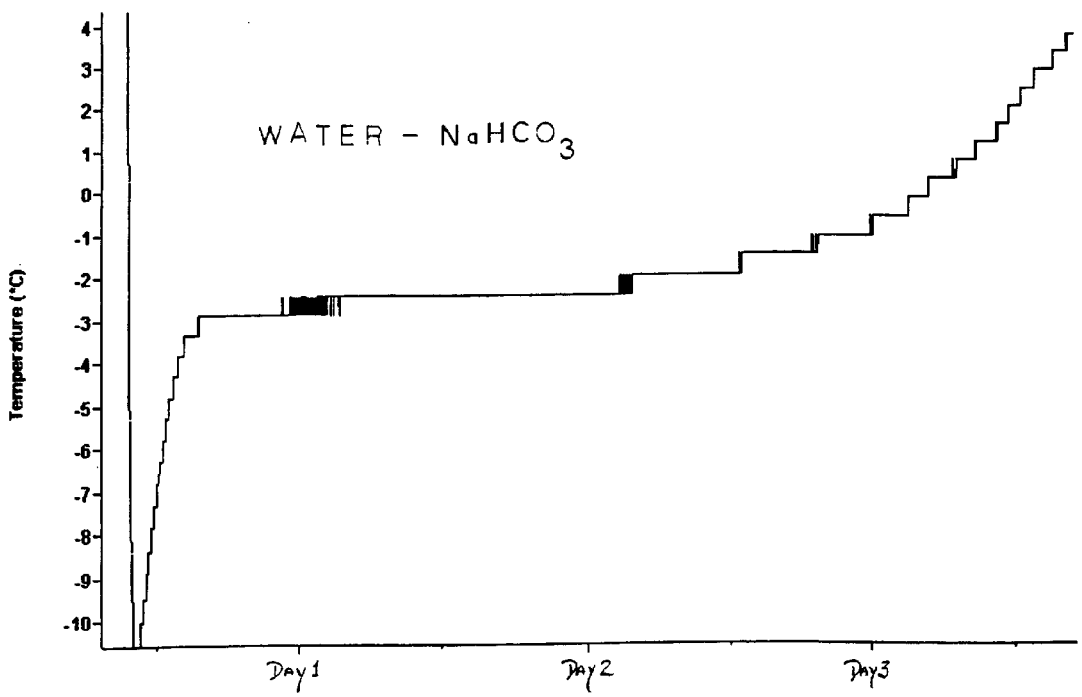

An example for a preferred solute for the present invention is sodium bicarbonate. The basis for selection of sodium bicarbonate as a preferred solute is the fact that it shows what can be termed a limited hysteresis during the melting event over at least some other solutions made from other solutes. For example, if it is determined that solutions having melting temperatures of −2.2° C. must be prepared, then the van't Hoff law predicts that 1.2 molal solutions must be prepared. Continuing with this example, both sucrose and sodium bicarbonate-water 1.2 molal solutions were prepared. Equal masses of these solutions were frozen and then allowed to melt with constant rates of heat being provided to each frozen sample while the temperatures of the samples were very accurately recorded against time. The respective time-temperature records are shown in FIG. 2 (sucrose) and FIG. 3 (sodium bicarbonate). The slopes of the time-temperature curves between these two records during the melting event show there to be differences between the sucrose and sodium bicarbonate. The reduced slope for the sodium bicarbonate solution temperature rate change during the melting event when latent heat is absorbed demonstrates the above cited limited hysteresis characteristic. Consequently, as shown at least by the time-temperature curves for 1.2 M sodium bicarbonate solutions as opposed to sucrose solutions, the sodium bicarbonate solutions are preferable because they maintain a more constant temperature during the melting event when heat is absorbed to provide latent heat for melting than do sucrose solutions.

This invention utilizes the combination of latent heat and melting point adjustment for a unique method and product. For preferred aqueous solutions, the rule of colligative properties provides an efficient method to relate melting temperatures with solution concentrations; namely, a linear relationship that predicts the amount of dissolved solute required to establish the temperature at which the solution when frozen will melt. This relationship provides prediction and control of the storage temperature provided by packs filled with such frozen solutions over the duration of their melting, i.e. when heat is absorbed to provide latent heat. The intake of excess heat to provide latent heat extends over a period of time when a pack maintains a stable preselected temperature. This period of time is up to 144 times longer, when measured in terms of absorbed heat rate, than the period of time over which a sensible heat coolant can provide stable temperatures.

Using molal control of solution melting temperatures permits very precise temperature control. In fact thermal stability on the order of ±0.1° C. is readily feasible. Even greater precision is feasible and is within the scope of the invention. Most importantly it is possible to construct a pack to provide a stable environment at any temperature over the range from at least less than 0° C. to −15° C. using the appropriate mole fraction. Solutions for packs of the present invention can be made from any water soluble solute combination. Various salts, polysacharides, proteins and polyhydroxy alcohols or any other solutes that dissolve in water may be used for solution formulation. Some examples include sodium chloride, calcium chloride, sodium bicarbonate, sucrose, fructose, sorbitol, glycerol, alanine, proline, etc. Some water soluble substances, such as sodium bicarbonate, have preferred physical/chemical characteristics pertaining to the absorption of heat during melting, as is discussed above, that makes them more suitable for applications in the food industry and in medical applications where maximum thermal stability is needed.

As another feature, a gelling agent may be added to a solution to prevent leakage of the solution from a pack, such as pack 10, in the event it is punctured. An acceptable gelling agent for the present invention is E 4 M a product sold by Dow Chemical, Co., Wilmington, Del. In this case, as in other cases when more than one solute is used, the molecular weight and mole fraction of each substance must be taken into account in the predictive calculation of melting temperatures, as well as possible chemical interactions between the solutes. In cases where no molecular weight for a product is available (e.g. molasses) the density (specific gravity) of the substance can be determined and used in the predictive (melting temperature) calculation.

Although the present invention has been described in considerable detail with reference to certain preferred embodiments thereof, other embodiments or configurations are possible. Accordingly, the spirit and scope of the appended claims should not be limited to the description of the preferred embodiments contained herein.

What is claimed is:

1. A method for maintaining a substance at a cold storage temperature, comprising the steps of:

selecting a cold storage temperature to be maintained;

preparing a thermal control material having a melting temperature equal to the selected cold storage temperature by determining a molality for a solution whereby the solution of that molality will have a melting temperature equal to the selected cold storage temperature, said thermal control material being the solution;

filling a pack with the prepared thermal control material and sealing the pack; and freezing the prepared thermal control material in the pack.

2. The method according to claim 1, further comprising the step of:

allowing the pack temperature to rise to the cold storage temperature.

3. The method according to claim 1, wherein the solution is an aqueous solution having a solute that is colligative.

4. The method according to claim 3, wherein the solute is sodium bicarbonate.

5. The method according to claim 1, further comprising the steps of:

unsealing the pack and draining out the thermal control material;

selecting a second cold storage temperature to be maintained;

preparing a second thermal control material having a melting temperature equal to the second selected cold storage temperature;

filling the pack with the prepared second thermal control material and resealing the pack; and freezing the prepared second thermal control material in the pack.

6. The method according to claim 5, wherein the second thermal control material is an aqueous solution having a solute that is colligative.

7. The method according to claim 1, wherein the selected cold storage temperature is 0.1° C. above a melting temperature of the substance being stored.

8. The method for preparing a pack containing a thermal control material that can be frozen to provide a specified cold storage temperature for a substance being stored, comprising the steps of:

selecting a cold storage temperature to be maintained preparing a thermal control material having a melting temperature equal to the selected cold storage temperature by determining a molality for a solution whereby the solution of that molality will have a melting temperature equal to the selected cold storage temperature, said thermal control material being a solution; and filling the pack with the prepared thermal control material and sealing the pack.

9. The method according to claim 8, wherein the solution is an aqueous solution having a solute that is colligative.

10. The method according to claim 9, wherein the solute is sodium bicarbonate.

11. The method according to claim 8, further comprising the steps of:

unsealing the pack and draining out the thermal control material;

selecting a second cold storage temperature to be maintained;

preparing a second thermal control material having a melting temperature equal to the second selected cold storage temperature; and filling the pack with the prepared second thermal control material and resealing the pack.

12. The method according to claim 11, wherein the second thermal control material is an aqueous solution having a solute that is colligative.

13. The method according to claim 8, wherein the selected cold storage temperature is 0.1° C. above a melting temperature of the substance being stored.

* * * * *